12) United States Patent
Xu et al.

(10) Patent No.: US 8,557,945 B2
(45) Date of Patent: Oct. 15, 2013

(54) KIND OF BIODEGRADABLE POLYESTER AND ITS PREPARATION METHOD

(75) Inventors: Yibin Xu, Guangdong (CN); Renxu Yuan, Guangdong (CN); Tongmin Cai, Guangdong (CN); Jian Jiao, Guangdong (CN); Shiyong Xia, Guangdong (CN); Zhimin Yuan, Guangdong (CN)

(73) Assignees: Kingfa Science & Technology Co., Ltd, Guangzhou (CN); Shanghai Kingfa Science & Technology Co., Ltd, Shanghai (CN)

( * ) Notice: Subject to any disclaimer, the term of this patent is extended or adjusted under 35 U.S.C. 154(b) by 0 days.

(21) Appl. No.: 12/744,278

(22) PCT Filed: May 15, 2009

(86) PCT No.: PCT/CN2009/071805
§ 371 (c)(1),
(2), (4) Date: Apr. 18, 2011

(87) PCT Pub. No.: WO2010/130098
PCT Pub. Date: Nov. 18, 2010

(65) Prior Publication Data
US 2011/0190468 A1 Aug. 4, 2011

(51) Int. Cl.
C08G 63/60 (2006.01)
C08G 18/80 (2006.01)
C08G 18/38 (2006.01)
C08G 63/183 (2006.01)

(52) U.S. Cl.
USPC .......... 528/45; 528/76; 528/73; 528/289; 528/296; 528/301

(58) Field of Classification Search
None
See application file for complete search history.

(56) References Cited

U.S. PATENT DOCUMENTS

| | | | | |
|---|---|---|---|---|
| 2,845,402 A * | 7/1958 | Woodruff | | 528/301 |
| 5,102,766 A * | 4/1992 | Nanya et al. | | 430/108.11 |
| 5,436,104 A * | 7/1995 | Yasuda et al. | | 430/124.1 |
| 5,466,553 A * | 11/1995 | Okutani et al. | | 430/109.4 |
| 5,677,049 A * | 10/1997 | Torii | | 428/32.73 |
| 5,786,408 A * | 7/1998 | Kuroda et al. | | 523/124 |
| 6,303,677 B1 * | 10/2001 | Warzelhan et al. | | 524/291 |
| 6,414,108 B1 * | 7/2002 | Warzelhan et al. | | 528/272 |
| 2003/0100645 A1 * | 5/2003 | Ahmed et al. | | 524/306 |
| 2003/0212244 A1 * | 11/2003 | Hayes et al. | | 528/296 |
| 2007/0104951 A1 * | 5/2007 | Ito | | 428/402.2 |
| 2008/0145775 A1 * | 6/2008 | Vijayendran et al. | | 430/109.3 |
| 2008/0153027 A1 * | 6/2008 | Veregin et al. | | 430/113 |

* cited by examiner

Primary Examiner — Randy Gulakowski
Assistant Examiner — Jeffrey Washville
(74) Attorney, Agent, or Firm — Sughrue Mion, PLLC

(57) ABSTRACT

The present invention relates to a kind of biodegradable polyester and its preparation method, which belongs to the field of biodegradable co-polyester product technology. The number-average molecular weight of the biodegradable polyester material under this invention is 6000-135000 g/mol, the molecular weight distribution is 1.2-6.5, and the range of crystallization temperature is 15° C.-105° C., which could overcome the disadvantages of existing technical products and can be processed into membrane materials, sheet materials and foam materials. During processing, the picking property will be dramatically changed with the appearance quality improved; after heat resistance is improved, this new type of polyester material could also be applied to the processing course with long cycles, for example, the injection processing course, and the biodegradable aliphatic/aromatic polyester materials provided by this invention has excellent mechanical properties.

19 Claims, No Drawings

KIND OF BIODEGRADABLE POLYESTER AND ITS PREPARATION METHOD

CROSS REFERENCE TO RELATED APPLICATIONS

This application is a National Stage of International Application No. PCT/CN2009/071805, filed May 14, 2009, the content of which is incorporated herein by reference in its entirety.

BACKGROUND OF THE INVENTION

1. Technical Field

The present invention relates to a kind of biodegradable polyester and its preparation method, which belongs to the field of biodegradable co-polyester product technology.

2. Description of Related Art

Biodegradable polymer is a kind of polymer material that may decompose into carbon dioxide and water under appropriate environmental conditions over a certain period. The degradation process is normally divided into two steps: first, the molecular weight of macro molecules decreases by hydrolysis and light/oxygen degradation, then it is further consumed by microorganisms. The microorganisms could be bacteria, fungi, microzyme and algae. A kind of testing method for biodegradability is provided in the international standard ISO14855, which is a relatively authoritative testing method in the testing of biodegradability for plastic materials. Various countries and regions define their own plastics degradation tests and testing standards according to the testing conditions and results, including the EN13432 testing standard developed by EU, the ASTM D6400 of U.S.A, the GB/T 19277 of China, etc.

Polyhydroxyalkanoate (PHA), for example, polylactic acid (PLA), polyhydroxybutyrate (PHB), polycaprolactone (PCL), poly-hydroxybutyrate-valerate (PHBV), has a history over 30 years, all of which, except PCL, could be obtained by biosynthesis with biodegradability (M. Kunioka et al, *Appl. Microbiol. Biotechnol.*, 30, 569, 1989). It is also pointed out by some reports that the polyester obtained from condensation polymerization of aliphatic dibasic acid (or ester) and dibasic alcohol also has biodegradability (written by J. M. Sharpley et al, "Application Science", 1976, p. 775). All the polyester materials obtained completely from aliphatic dibasic alcohol and dibasic acid have relatively low melting points and vitrification temperatures, and there are defects in their application.

Aromatic polyester, for example, polyethylene terephthalate (PET), polybutylene terephthalate (PBT), etc., is the plastic material with very wide application; however, such materials have no degradability (Kirt-Othmer Encyclopedia of Chemical Technology, Suppl. Vol., Wiley-Interscience, New York, 1984, p. 626-668). In early 1980's, there was relevant report pointing out the viewpoint of Y. Tokia and T. Suzuki in some article (Nature, 270, 76-78, 1977; Journal of Applied Polymer Science, 26, 441-448, 1981) that the aliphatic polyester obtained from the condensation polymerization of succinic acid and aliphatic dibasic alcohol could be degraded by enzyme; however, the polyester formed by aromatic dibasic acid and aliphatic dibasic alcohol, for example, PBT and PET, could not be degraded by enzyme; the block copolyester resulting form PCL and PBT could be degraded by enzyme.

In Patent WO 92/13019, a kind of polyester copolymer formed by aromatic dibasic acid and aliphatic dibasic alcohol has biodegradability. The structure of such copolyester requires that the dibasic alcohol segment with the minimum molar ratio of 85% in the polyester contains one terephthalic acid segment. To improve the material hydrophilic property and reduce crystallization, it is proposed by this patent to introduce metal salt of dimethyl isophthalate-5-sulfonic acid with the molar ratio of 2.5% or dibasic alcohol unit containing ether structure of chain scission into the copolymer structure. However, the patent has no microorganism degradation results of the material; only the water-boiling test was carried out, and the mechanical property of the material is not satisfactory.

It is revealed by U.S. Pat. No. 5,292,783 and U.S. Pat. No. 5,446,079 the block and linear irregular copolyester obtained by condensation polymerization with aliphatic dibasic acid and aromatic dibasic acid as repetitive units. Such material has the biodegradability. Among others, the dibasic carboxylic acid consists of 5-65% (molar ratio) aliphatic dibasic acid and 35-95% (molar ratio) aromatic dibasic acid, and the dibasic alcohol is aliphatic dibasic alcohol. However, since the materials have relatively low melt viscosity and melt strength, they cannot be applied in the intrusion processing field, for example, it is relatively difficult to use the material for film blowing, foaming and flow casting.

U.S. Pat. No. 5,661,193 reveals a kind of aliphatic acid—aromatic acid copolyester with a branching and irregular structure, which has the biodegradability. It is used to produce foam material. The polyester consists of 30-95% (molar ratio) polycondensate units of aliphatic dibasic acid, 5-70% (molar ratio) polycondensate units of aromatic dibasic acid, and the dibasic alcohol units in the polycondensate units are polycondensate units of aliphatic dibasic alcohol. The content of branching agent is 0.01-10% of the weight of dibasic acid used for polymerization. The branching agent revealed in the patent is multi-carboxyl aliphatic acid and (or) anhydride, multi-carboxyl aromatic acid and (or) anhydride, multi-hydroxyl aliphatic alcohol and hydroxyl isocyanurate.

Patent EP A565235 proposes a kind of aliphatic copolyester containing amino formyl structural units (—NH—C(O)O—). The basic units for the copolyester are succinic acid and aliphatic dibasic alcohol, which have the biodegradability. To change the defect of relatively low molecular weight resulting from condensation polymerization of pure aliphatic acid and alcohol, diisocyanate reaction units are introduced into the reaction. However, diisocyanate reaction unit is easy to generate gelling point in the reaction, it is relatively difficult to control the reaction, and the appearance of gel will impact the performance of the material.

U.S. Pat. No. 6,018,004 also reveals several kinds of polyester materials, which also have biodegradability. Among others, the polycondensate units of dibasic acid in a kind of biodegradable polyester consist of 35-95% (molar ratio) polycondensate units of aliphatic dibasic acid, 5-65% (molar ratio) polycondensate units of phthalandione and 0-5% (molar ratio) sulfonate, in which the polycondensate units of dibasic alcohol are alkyl dibasic alcohol and cycloalkyl dibasic alcohol. The above-mentioned composition of the polyester could form another kind of copolyester with biodiagradability with the following structure: chemical substances containing hydroxyl and carboxyl with over three functional groups at the molar ratio of 0.01-5% (take the total mole number for the polycondensate units of dibasic acid as 100). The patent has relatively detailed definition for such substances, including aromatic polybasic acid, aliphatic polybasic acid, aliphatic polybasic alcohol, aromatic hydroxyl acid, etc; the structure could also be diisocyanate-type chemical substances with the weight percentage of 0.1-5%. The patent also defines such substances in details, including aromatic diisocyanate and aliphatic diisocyanate.

U.S. Pat. No. 6,120,895 reveals a kind of polyester material with biodegradability. The polyester material consists of two parts, Component A with the molar ratio of 95-99.9% and Component B with the molar ratio of 0.01-5%: Component A consists of the chemical substances including 20-95% (molar ratio) aliphatic dibasic acid (or its ester), 5-80% (molar ratio) aromatic dibasic acid (or its ester) and dibasic hydroxyl and amido alcohols; Component B consists of single-cluster or multi-cluster isocyanate chemical substances. The preparation method has both the characteristics of polycondensation reactions and solidification reaction for polyester. The dibasic alcohol used in Component A is aliphatic dibasic alcohol or polyether dibasic alcohol. Although the introduction of isocyanurate may raise the heat-resistant property of the material, the isocyanurate defined in the patent makes reaction control very difficult with many gelling points.

Up to now, the biodegradable polyester resin materials could not meet the preparation requirements, especially in terms of the requirements on the performance and production requirements of membrane material. Even with chain extension or branching treatment during synthesis, the aliphatic polyester still has a relatively low melting point, insufficient heat resistance and picking defect during processing. The linear aliphatic/aromatic copolyester with diisocyanate chain extension treatment is easier for the processing of membrane materials compared with the polyester materials without chain extension treatment, but the formed gel particles will interfere with the processing of membrane materials, especially when the cycle period extends, and the mechanic properties is relatively poor.

BRIEF SUMMARY OF THE INVENTION

The objectives of this invention are to overcome the shortcomings of existing technology and provide a biodegradable aliphatic/aromatic polyester material with better appearance quality, heat resistance and good mechanical properties. The mentioned polyester material could be used as the material for the preparation of membrane materials, which significantly changes the picking property with wide application scope.

Another objective of this invention is to provide the preparation method for the above-mentioned polyester material.

The above objectives are realized by this invention through the following technical scheme:

A kind of biodegradable polyester produced with 94-100% (molar ratio) Component A and 0-6% (molar ratio) Component B; the number-average molecular weight of the mentioned Component A and Component B is 6000-135000 g/mol, the intrinsic viscosity is 0.6-1.8 dl/g (the solute is the phenol-carbon tetrachloride mixing system with the mass ratio of 7:3, and the polyester solubility is 0.01 g/ml), the molecular weight distribution is 1.2-6.5 and the crystallization temperature range is 15° C.-105° C.

The mentioned Component A consists of Component A1 and Component A2 at the molar ratio of 0.35-1.6:1;

The mentioned Component A1 consists of Component A11 at a molar percentage of 20-100% and Component A12 at a molar percentage of 0-80%;

The mentioned Component A11 is any of the following substances or the mixture made up of more than two kinds of the following substances, that is, aliphatic dibasic acid, cyclic aliphatic dibasic acid, esterified derivatives of aliphatic dibasic acid and esterified derivatives of cyclic aliphatic dibasic acid; or it is the mixture consisting of two or more than two kinds of aliphatic dibasic carboxyl acid and/or cyclic aliphatic dibasic acid or their ester with different chain length; the mentioned aliphatic dibasic acid and cyclic aliphatic dibasic acid with the preferred carbon atom number of $C_4$-$C_{18}$, especially any of or the mixture made up of more than two kinds of the following dibasic acids or their esters: oxalic acid, succinic acid, glutaric acid, adipic acid, azelaic acid, sebacic acid, tridecanedioic acid, maleic acid, 1,1 cyclo-butane-dicarboxylic acid, 1,1-cyclo-hexane diacetic acid, 1,4-cyclo-hexane diacetic acid, cyclo-hexane-1,2, norbornane-2,3-dicarboxylic acid or amadantane diacetic acid.

The mentioned Component A12 is any of the following substances or the mixture made up of more than two kinds of the following substances: aromatic dibasic acid or ester of aromatic dibasic acid; or it could be a mixture consisting of two or more than two kinds of aromatic dibasic carboxylic acid or their ester with different chain length; the mentioned aliphatic dibasic alcohol or ester of aromatic dibasic acid is the dibasic acid or their ester with the preferred carbon atom number of $C_4$-$C_{18}$, especially selected from any of or the mixture made up of more than two kinds of the following dibasic acids or their esters: terephthalic acid, phthalic acid, isophthalic acid, p-phenylenediacetic acid and o-phenylenediacetic acid.

The mentioned Component A2 consists of Component A21 at a molar percentage of 80-99.9% and Component A22 at a molar percentage of 0.1-20%;

The mentioned A21 consists of at least one of the following substances: aliphatic dibasic alcohol with carbon atom number of $C_2$-$C_8$, cyclic aliphatic dibasic alcohol with carbon atom number of $C_5$-$C_{16}$, polycyclic aliphatic dibasic alcohol, aliphatic polyether dibasic alcohol, and hydroxyl aliphatic acid; it can also consist of at least one kind of the following substances: aliphatic dibasic alcohol, cyclic aliphatic dibasic alcohol, aliphatic polyether dibasic alcohol and hydroxyl aliphatic acid with different lengths of carbon chain; the mentioned aliphatic polyether dibasic alcohol is aliphatic dibasic alcohol with the preferred carbon atom number of $C_2$-$C_8$, especially selected from any of or the mixture consisting more than two kinds of the following dibasic alcohols: glycol, 1,2-propanediol, 1,3-propanediol, 1,2-butanediol, 1,4-butanediol, 1,5-pentanediol, 2,2-dimethyl-1,3-propanediol, 2-ethyl-2-tert-butyl-1,3-propanediol, 2,2,4-trimethyl-1,6-hexanediol; the mentioned aliphatic dibasic alcohol is cyclic aliphatic dibasic alcohols or polycyclic aliphatic dibasic alcohols with the carbon atom number of $C_5$-$C_{16}$, especially selected from any of or the mixture consisting of more than two kinds of the following dibasic alcohols: 1,3-cyclopentanediol, 1,4-cyclo-hexanediol, 1,2-cyclo-hexanedimethanol, 1,3-cyclo-hexanedimethanol, 1,4-cyclo-hexanedimethanol, isosorbide. The scope of molecular weight for the mentioned aliphatic polyether dibasic alcohol is 25-12000 g/mol, the preferred scope of molecular weight is 500-4500 g/mol. It is preferred to select the aliphatic polyether dibasic alcohol from any of or the mixture consisting of several kinds of the following polyether dibasic alcohols: dimmer of ethylene oxide, trimer of ethylene oxide, polyethylene oxide, polypropylene oxide, poly(tetramethylene ether glycol), ethylene oxide-propylene oxide copolymer; it is preferred to select the mentioned hydroxyl aliphatic acid from the hydroxy organic acids with the carbon atom number of $C_4$-$C_{18}$, especially from any of or the mixture consisting of more than two kinds of the following hydroxy organic acids: glycolic acid, α-hydracrylic acid, β-malic acid, β-hydroxy-butyric acid, hydroxy-butanedioic acid, 5-hydroxy-valeric acid, 3-hydroxy-hexanoic acid, 5-hydroxy-hexanoic acid, 6-hydroxy-hexanoic acid, 7-hydroxy-heptanoic acid, 3,5-di-hydroxy-heptanoic acid, hydroxy-octanoic acid, 5-hydroxy-decanoic acid, 5-hydroxy-dodecanoic acid, 9,10,16-trihydroxy-hexadecanoic acid, 3,4-dihydroxy-cinnamic acid, p-hydroxy-cinnamic acid, agaric acid or their polymers.

The mentioned A22 consists of at least one of the following substances: dibasic alcohol containing aromatic nucleus, polyether dibasic alcohol containing aromatic nucleus or hydroxyl organic acid containing aromatic nucleus with carbon atom number of $C_8$-$C_{18}$; it could also consist of at least one of the following substances: dibasic alcohol containing aromatic nucleus, polyether dibasic alcohol containing aromatic nucleus and hydroxyl aliphatic acid containing aromatic nucleus with different lengths of carbon chains;

Both the mention dibasic alcohol containing aromatic nucleus and polyether dibasic alcohol containing aromatic nucleus have the molecular structure as shown in Formula 1:

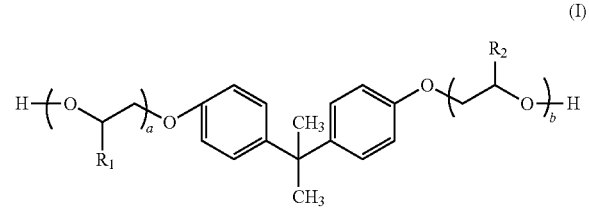

(I)

In Formula I, $R_1$ could be —H, —$CH_3$ or —$C_2H_5$; $R_2$ could be —H, —$CH_3$ or —$C_2H_5$, a and b are both numerals selected from any positive number satisfying the condition of "a+b=2~30" or 0; the mentioned dibasic alcohol or polyether dibasic alcohol could be obtained by the etherification of alkylene oxide with the help of catalyst and with biphenol A as the starting reactant.

The mentioned polyether dibasic alcohol in Component A22 is preferred to be selected from any of or the mixture consisting of more than two kinds of the following polyether dibasic alcohols: dimmer of ethylene oxide, trimer of ethylene oxide, polyethylene oxide, polypropylene oxide, poly (tetramethylene ether glycol), ethylene oxide-propylene oxide copolymer; the scope of molecular weight for the mentioned aliphatic polyether dibasic alcohols is 25-12000 g/mol, and the preferred scope of molecular weight is 500-4500 g/mol; the mentioned hydroxy organic acid containing aromatic nucleus is the hydroxy organic acids containing aromatic nucleus with the carbon atom number of $C_8$-$C_{18}$, especially selected from any or the mixture consisting of more than two kinds of the following hydroxy organic acids: o-hydroxybenzoic acid, p-hydroxybenzoic acid, 2,4-dihydroxybenzoic acid, 4-hydroxy phthalate or its derivatives, 4-hydroxy-o-phthalic anhydride or the polymers of the above-mentioned organic acids.

The mentioned Component B consists of any of the following substances or the mixtures made up of more than two kinds of the following substances at any mass ratio: Component B1, Component B2 and Component B3;

The mentioned Component B1 is any of the following substances or the mixtures made up of more than two kinds of the following substances: aliphatic or aromatic polybasic alcohol and aliphatic or aromatic polybasic acid; the mentioned mixture is preferred to be a mixture consisting of any two or more than two kinds of the following substances: glycerin, tri(hydroxymethyl) propane, sorbitol, glucose, glucoside, pentaerythritol, dipentaerythritol, polyether triols, polyether tetrahydroxy alcohol, pyromellitic acid, pyromellitic acid dianhydride, trimesic acid, benzenetricarboxylic acid (1,2,4-benzene-tricarboxylic acid), tartaric acid, citric acid, citric anhydride or ester derivatives of the above-mentioned compounds; the mentioned polyether tribasic alcohol is obtained by using glycerin and trimethylolpropane as the precursors and etherifying with alkylene oxide under the effects of catalyst. The scope of molecular weight for the obtained polyether tribasic alcohol is 200-12500 g/mol, and the preferred scope of molecular weight is 400-3500 g/mol.

The mentioned aliphatic polyether polybasic alcohol in Component B1 of this invention is preferred to be selected from polyether tetrahydroxy alcohol, and the mentioned polyether tetrahydroxy alcohol has the molecular structure as shown in Formula II:

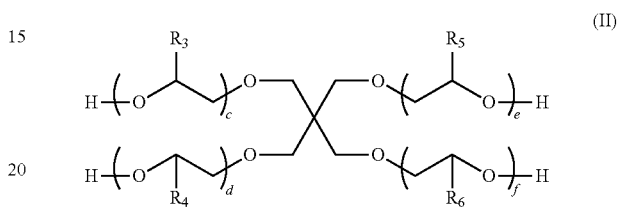

(II)

In which, $R_3$, $R_4$, $R_5$ and $R_6$ could be same or different, which are all —H or —$CH_3$; c, d, e and f are numerals, which are selected from any of the positive numbers satisfying the condition of "c+d+e+f=4~30"; the mentioned polyether tetrahydroxy alcohol is obtained by the etherification of alkylene oxide with the help of catalyst and with pentaerythritol as the starting reactant.

The mentioned Component B2 is selected from any of the following substances or the mixture made up of more than two kinds of the following substances: isocyanate compounds, isocyanurate cyclic polybasic alcohol or isocyanate polyether polybasic alcohol; the mentioned isocyanate compounds are diisocyanate modified from carbonized diimine, dimmer or trimer of blocked isocyanate or diisocyanate; the mentioned diisocyanate is any of or the mixture consisting of more than two kinds of the following substances: toluene diisocyanate, diphenyl-methane-diisocyanate, m-xylylene-diisocyanate, isophorone-diisocyanate, hexamethylene-diisocyanate, 2,6-diisocyanate-methyl hexanoate, methyl-cyclo-hexane-diisocyanate, 2,2,4-trimethyl-hexane-diisocyanate, isopropylidene-bi-(cyclo-hexanediisocyanate-4), organo-silicone-diisocyanate or diphenyl-methane-diisocyanate containing carbonized diimine; the invention enables the self polycondensation reaction of isocyanate with organic phosphine as the catalyst and under the heating condition to generate the compound containing carbonized diimine group (—N═C═N—); the organic phosphine catalysts in common use include: penta-heterocyclic phosphine oxide, 1-phenyl-3-methyl-1-phosphinidene oxide, triethyl phosphate, triphenyl phosphine oxide, etc. Among other, penta-heterocyclic phosphine oxide has the best catalyzing effects with low dosage and low reaction temperature; with the effects of catalyst, part of the isocyanate monomers firstly convert to diisocyanate containing carbonized diimine structure. Such diisocyanate containing carbonized diimine structure could further react with isocyanate by addition and cyclization to generate diisocyanate containing uretonimine groups; the multi isocyanate of the above-mentioned structure not only is stable for storage and easy for use, but also could endow the materials with special spatial structure and flame-retarding effects.

In the mentioned diisocyanate modified with carbonized diimine, carbonized diimine accounts for 5%~30% (mass percentage) of the modified diisocyanate; the mentioned blocked isocyanate is formed by blocking isocyanate with phenol and caprolactam, which could combine with various polybasic alcohols and is stable under normal temperature. The blocking of isocyanate is to make isocyanate or the prepolymer containing dissociated isocyanate group react with some substances containing active hydrogen or the substances able to react with isocyanate group so as to deactivate the dissociated isocyanate group under normal temperature; that is, to realize the blocking of isocyanate group. Such blocking reaction is reversible under certain conditions; therefore, it is possible to enable the deblocking of blocked isocyanate group under certain conditions to exert the effects of isocyanate group. The blocking of diisocyanate is one kind of isocyanate blocking in common use. The mentioned blocked diisocyanate is the blocked isocyanate of toluene diisocyanate, diphenyl-methane-diisocyanate, m-xylylene-diisocyanate, isophorone-diisocyanate, hexamethylene-diisocyanate, 2,6-diisocyanate-methyl hexanoate, methyl-cyclo-hexane diisocyanate, 2,2,4-trimethyl hexane diisocyanate, isopropylidene bi(cyclo-hexanediisocyanate-4) or its solution; the mentioned blocking substance could be: phenol, alcohol, lactam, dicarbonyl compound, oxime, pyrazole, sodium bisulfite; catalyst could be used for the deblocking of the mentioned blocked isocyanate.

The mentioned blocked isocyanate in the invention is particularly any kind of or the mixture consisting of several kinds of the following blocked diisocyanate with different solution concentrations: toluene diisocyanate blocked by diacetylmonoxime, toluene diisocyanate blocked by alcohol, toluene isocyanate blocked by caprolactam, hexa-methylene diisocyanate blocked by diacetylmonoxime, hexa-methylene diisocyanate, adipic dinitrile carbonate and trimethylamine methacrylimide blocked by caprolactam.

The mentioned isocyanate dimers are dimmer of aromatic isocyanate, which are particularly dimer of toluene diisocyanate and dimmer of diphenyl-methane-diisocyanate with different solution concentrations. Both aromatic isocyanate and aliphatic isocyanate could have dimerization reaction. When isocyanate dimerizes, the factors affecting the dimerization include the activity of isocyanate groups, reaction temperature, etc. The common dimerization catalysts include phosphine compounds and tertiary amine. uretidione ring generated by dimerization has relatively poor heat stability, which could be easily dedimerized under heating conditions. Making use of this characteristic, a dimmer is often used as crosslinking agent in the preparation of polyurethane. Since it has higher storage stability under normal temperature compared with monomer, it could be mixed with other compounds containing active hydrogen under normal temperature, and it can decompose into isocyanate monomers with heating and catalyst to complement the required reaction.

The mentioned isocyanate trimer is any of or the mixture consisting of more than two kinds of the following solutions with different concentrations: trimer of toluene diisocyanate, trimer of hexa-methylene diisocyanate, trimer of poly isocyanate I, mixed trimer of hexa-methylene diisocyanate-toluene diisocyanate, and the mixture containing the above-mentioned substances with different contents, especially isocyanate trimer solutions with different concentrations. Both aliphatic isocyanate and aromatic isocyanate could form trimers under appropriate conditions to obtain the derivatives containing isocyanurate heteroatomic rings. The same isocyanate monomers could have a trimerization reaction, and the mixed system consisting of two or more than two kinds of isocyanate monomers could also have trimerization reaction. The isocyanurate heteroatomic rings generated in the trimerization of isocyanate are very stable with flame retarding properties. Only high temperature could damage the structure of isocyanurate heteroatomic rings. When isocyanate trimerizes, the factors affecting the trimerization reaction include the activity of isocyanate groups, catalyst, reaction temperature, etc. There are many kinds of catalysts for the trimerization of isocyanate. The catalysts applicable to the trimerization of aromatic and aliphatic isocyanate include dissoluble sodium alcoholate or potassium salts, for example, sodium caprylate, potassium benzoate, potassium salicylate, sodium phenolate, sodium sodium methoxide, sodium oxalate, etc.; for the compounds of the nitrogen family elements and organic metallic compounds, in order to control the trimer content and prevent polymer generation, the reaction could be terminated by controlling the temperature of the reaction system and adding polymerization inhibitor at appropriate stage of the reaction. Even in this case, the obtained polymer system is still the mixture containing certain amount of polymers which are mostly trimers. The polymerization inhibitors in common use include benzoyl chloride, phosphoric acid, p-toluene-sulfonate, dimethyl sulfate, etc. The isocyanate trimer containing isocyanurate cyclic structure has the advantages of low volatility, low toxicity and high functionality. The heterocyclic structure of isocyanurate also endows the materials with heat resistance, flame retarding properties and chemical resistance.

The above-mentioned substances containing isocyanate functional groups could be prepared into the solutions with different concentrations before use so as to enable easy operation of addition and mixing process and homogeneous dispersion and distribution. The solvents in common use include toluene, petroleum ether of different boiling points, etc. The concentration scope of the added solvents in the above solutions is related to the viscosity of the substances containing isocyanate functional groups. The preferred scope of solution concentration is 15%-95% (weight percentage).

Both the mentioned isocyanurate cyclo polybasic alcohol and isocyanurate cyclo polyether polybasic alcohol in Component B2 for this invention has the molecular structure as shown in Formula III:

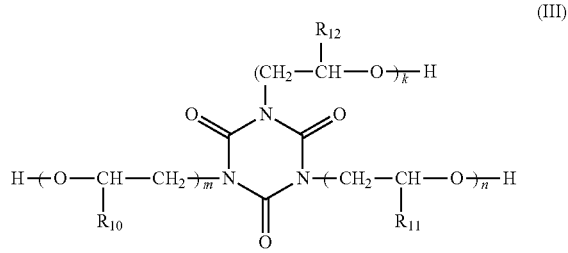

In which, $R_{10}$, $R_{11}$ and $R_{12}$ may be same or different, which are all —H, —$CH_3$ or —$CH_2CH_3$; m, n and k are numerals selected from any of the positive numbers satisfying the condition of m+n+k=3~30; The isocyanurate cyclo polybasic alcohol and isocyanurate cyclo polyether polybasic alcohol could be obtained by following the method below: with isocyanurate (whose synthesis method has been present above) as the initiator, boron trifluoride ethylether complex as the catalyst and epoxy compounds as the ring unit, the isocyanurate cyclo polybasic alcohol and isocyanurate cyclo polyether polybasic alcohol could be obtained through cationic ring-opening reaction.

The mentioned Component B3 is selected from carbonized diimine compounds; the mentioned carbonized diimine compound is the carbonized diimine monomers or carbonized diimine polymers with different solution concentrations which have 1-30 carbonized diimine groups in their molecular structure with the molecular weight of 40-30000 g/mol. It can also be mixed by two or more than two kinds of substances with the above-mentioned characteristics and with different molecular weight and different contents of carbonized diimine groups at any ratio. Currently the relatively mature method for the preparation of carbonized diimine or its polymers is to generate it by heating isocyanate with the effects of catalysts. With the improvement of reacting solvents, for example, by using halogenated hydrocarbon, alphatic cyclic ether, mixed solvent or not using solvents, the poly-carbonized diimine solution or powder with high molecular weight could finally be obtained with good storage stability. Diisocyanate generates linear poly-carbonized diimine, however, the isocyanate with the functionality above 3 generates poly-carbonized diimine with branched structure. This kind of polycondensate has a very high melting temperature. Poly-carbonized diimine has good heat resistance and high activity, which could react with many substances with wide applications. In the biodegradable polyester, the substances of carbonized diimine are used, which could also effectively adjust the degradation cycle of the materials.

In the existing technologies, the thermoplastic polyester is the polymer obtained through the polycondensation reaction of dibasic alcohols and dibasic acids. The dibasic acids and dibasic alcohols of different kinds could synthesize many kinds of polyester with different characteristics. The major commercialized varieties mainly include: polybutylene terephthalate, polyethylene terephthalate, poly terephthalate-1,4-cyclo-dimethyl hexane, polyethylene naphthalate and polyester liquid crystalline polymer series, polyarylate, polyester elastomer, etc. Depending on the polyester varieties and manufacturers, there are differences in terms of synthesis preparation process and synthesis methods. Generally, the production of polyester is divided into two types: intermittent production process and continuous production process. Fundamentally, the chemical process of polyester synthesis consists of esterification phase, ester exchange phase and polycondensation phase. Depending on polyester varieties and synthesis control methods, the equipment configuration and process requirements for each phase have their own characteristics.

The biodegradable polyester of this invention belongs to thermoplastic polyester, whose preparation method consists of esterification phase, ester exchange phase and polycondensation phase. The mentioned Component B may be added at any of the mentioned reaction phases, that is, it may be added before or after the esterification phase (which is also called an ester exchange reaction), before or after the polycondensation reaction, or during post-processing; Component B could be either all added at one time or added by several times. The addition by several times could be the addition by several times before, after and during different reaction phases or the addition by several times before, after or during any of the reaction phases. The different timing for the addition by several times has no impact on the final degradation performance of the materials. The biodegradable polyester with different application characteristics could be obtained by selecting the way of addition for Component B based on the specific needs. For the mentioned post processing, such as mechanical mixing and processing, single-screw processing, double-screw processing or other existing processing methods, the process conditions for the preparation method of this invention could refer to existing technologies. As the preferred option, the temperature scope for the esterification and ester exchange reaction phase of the preparation method in this invention is 150-240° C., the reactions could take place under normal pressure, and the polycondensation could take place with pressure reduction between 160 and 250° C.

The principle for the preparation method of this invention is to obtain polyester materials by polycondensation, which is also relatively mature control process. It basically consists of three processes based on Component A as the main basic material: esterification phase, ester exchange phase and polycondensation phase. The advantage for the preparation method of this invention is that Component B can be added at any of the three above-mentioned phases, which could also be introduced into the polyester materials during thermal processing after the completion of polycondensation process to obtain the degradation products with broader performance.

The reactions could be catalyzed by adding a certain amount of catalysts during the reactions when preparing biodegradable polyester by polycondensation. These catalysts include the mixtures based on the elements of Ti, Ge, La, Ce, Zn, Fe, Mn, Co, V, Zr, Li, Ca, especially the organic metallic mixtures of these elements, for example, organic salts, alkoxy salts and acetylacetone salts of these elements. The deactivation of the catalysts should be avoided during addition.

During the polycondensation reaction, in order to avoid unnecessary degradation and/or branching reaction, certain amount of stabilizers could be added during the reactions. These stabilizers include: trialkyl phosphite, triphenyl phosphate, triphenyl phosphonate, trialkyl phosphonate. The use of phosphoric acid and phosphorous acid should be avoided to prevent any negative effects on catalysts.

The contents of catalysts added in the biodegradable polyester related to this invention are between 0.01% and 3% (weight percentage), and the content of 0.5%-2% (weight percentage) is preferred. For high efficient Ti catalysts, their addition could be control within one-millionth order of magnitude (weight percentage). When the reaction reaches the removal of redundant dibasic alcohols or the formation of oligomers, the catalysts are added. The catalysts could be added as the solution of certain concentration or certain mixture of the catalysts based on different elements.

The biodegradable polyester related to this invention could be applied in the plastic processing fields such as injection molding, blow molding, suction molding, flow casting, fiber pulling, etc. The operation can be carried out on conventional processing equipments, and it can also be commixed with other degradable plastics or vegetable-based materials, such as polylactic acid, polycaprolactone, polyglycolic acid, succinic acid/butanediol copolyester, starch, cellulose, vegetable fiber, vegetable powder, etc. It can also be mixed with common plastics to produce structural material pieces, sheets, membrane materials, foam materials and frame materials which are applied as the consumptive materials for the industries of packaging, transportation, catering and agriculture & pasturage.

The initial form of the biodegradable polyester prepared in this invention is the material without the limit of shape and dimension.

The biodegradable polyester prepared in this invention could be used to prepare packing membrane materials, and it can also be coated with the following processes: rolling coating (plastic rolling), knife coating (brush coating), spray coating or injection membrane, etc. The application of biodegradable polyester in these materials is not limited by the dimension and thickness of the carriers. The products include the coating products for paper, fiber or starch.

The biodegradable polyester prepared in this invention could produce the filature with different appearance characteristics with corresponding conventional spinning processes.

The filature can be processed by stretching, twisting, circular knitting, winding, oil applying and texturizing to obtain spinning products, satisfying the requirements of subsequent processing or use. The filature can be further processed into fiber on conventional processing equipments, and then woven into cloth or processed into the product with certain breathability. The filature can also be produced into silk and thread products of certain shape or functions without weaving, such as felt, silk beam, porous fiber (beam), silk beam for cigarettes, etc.

The biodegradable polyester of this invention can be added into fillers at a ratio of 0-85% based on the weight of biodegradable polyester basic material. The fillers could be one kind of or the mixture consisting of more than two kinds of the following substances: carbon black, white carbon black, starch, modified starch, wood powder, vegetable fiber, various linen, cellulose fiber, modified cellulose, wollastonite, various whisker, ferrous oxide, natural mineral filler, synthesized mineral filler, calcium carbonate, calcium sulfate, barium sulfate, titanium pigment, stabilizer, organic phosphine compounds or their derivatives, antioxidant, secondary amine compounds, UV stabilizer, lubricant, release agent, nucleating agent, organic pigment, inorganic pigment, organic color concentrate, inorganic color concentrate. Lubricants and release agents include aliphatic alcohols and organic salts such as calcium stearate or zinc stearate, mineral wax, vegetable wax, animal wax. The above-mentioned fillers can also be added into the biodegradable polyester as master batches. The addition process could be during the thermal processing of biodegradable polyester, for example, single-screw extrusion process and double-screw extrusion process, to obtain the particle material with the diameter above 2 mm for the application in the secondary molding process. They can also be mixed into the biodegradable polyester resin materials during physical mixing process based on the needs for direct application in secondary molding and processing.

The biodegradable polyester of this invention can produce products with adhesive properties by conventional methods. The biodegradable polyester can be used to prepare adhesives with biodegradation characteristics by the preparation process of conventional adhesives with the assistance of tackifiers such as natural resin. It can also be used to prepare adhesive products, such as hot melt adhesives, without solvent by conventional process.

The biodegradable polyester of this invention can be used to prepare foam materials by conventional methods. The bulk density of the foam material is 0.15-1.1 g/cm$^3$. The typical foam processing equipment consist of sing-screw extruder, injection component for liquid or gas foaming agent, molding die and supporting equipments. The length-diameter ratio of the extruder is 30:1. Another kind of conventional foam processing equipment consist of two sets of screw extrusion systems, one in the front and one behind. Since the dimension of the back screw may change depending on the needs, such equipment can be used for the processing of foam materials with a bigger size. There is no great difference for the processing methods of these two kinds of processing equipments, both of which could produce biodegradable polyester foaming materials. The biodegradable polyester and other fillers and auxiliaries are added from the discharge opening of the single-screw extruder. The foaming agent is injected by the injection system at the screw transmission section of the single-screw extruder with the amount about 0.1%-20% (weight) of biodegradable polyester. The ratio of 0.1%-5% is preferred. The foaming agents include one of or the mixture consisting of more than two kinds of the following substances: inert gases such as nitrogen gas, carbon dioxide; organics with the boiling point between −40° C. and 50° C., such as propane, butane, pentane, aether; reactive foaming agents, such as sodium bicarbonate, mixture of sodium bicarbonate and citric acid, azo compounds. The foaming agents are blended and dispersed into the biodegradable polyester melt in the screw extruder. The mixed melt is extruded from the die. After swelling, molding and cooling processes, it is collected by the accessorial processing system to obtain the section materials of biodegradable polyester.

Compared with existing technologies, the invention has also the following beneficial effects:

The biodegradable polyester of this invention is the polyester materials obtained by introducing the components of dibasic alcohols and (or) polybasic alcohols containing phenyl groups in the composition of aliphatic polyester and aliphatic/aromatic copolyester. The resultant not only endow polyester materials with biodegradation properties, but also changes the softness of polyester materials and improves the crystallization rate of the materials; the invention also prevents the generation of unnecessary gelling phenomenon during the processing of polyester materials after chain extension and improve the material stability under long processing period by introducing chain extender and (or) crosslinking agent with long chain characteristics into the biodegradable polyester materials; and there is a range of critical ratio for dibasic alcohol (polybasic alcohol) containing phenyl groups and chain extender (crosslinking agent) with long chain characteristics in polyester materials in the technical scheme of this invention, which it enables the materials certain self-adhesive characteristics and certain opening properties of membrane materials when satisfying the transparency requirements so that the requirements for some applications could be satisfied, for example, preservative film, self-sealing film, patches, adhesives, coating, etc.

The biodegradable polyester materials of this invention overcome the shortcomings of existing technical products. The polyester materials of this invention can be used for the processing of membrane materials. The processing will dramatically change the picking characteristics with better appearance quality; after the heat resistance is improved, the new polyester materials could also be applied to the processing course with long cycle, for example, injection molding process. The biodegradable aliphatic/aromatic polyester materials provided by this invention have good mechanical properties.

DETAILED DESCRIPTION OF THE INVENTION

The implementation examples are presented below to further detail the invention. However, it is noted that the invention is not limited to these implementation examples. Some nonessential changes and adjustments made for this invention by the professionals of this sector still belong to the protective scope of this invention.

The testing methods for relevant indicators in the implementation are as follows:
1. Determination of relative molecular mass: Use Waters gel chromatography to determine relative molecular mass of polymer with trichlormethane as mobile phase. The effluent rate is 1 mL/min, the temperature is 40° C., and the standard sample is polystyrene with narrow distribution;
2. Determination of intrinsic viscosity: Determine the intrinsic viscosity of the sample at 25° C. with Ubbelohde viscometer. Take the mixed solution of phenol and o-dichlorobenzene (with the mass ratio of 3:2) as the solvent. The sample concentration is 0.005 g/mL.

3. Determination of carboxyl-terminated content: Use the mixed solution of o-cresol and trichlormethane (with the mass ratio of 7:3) as the solvent. Determine the carboxyl-terminated content with metrohm Titrino automatic potentiometric titrator from Switzerland. The method refers to the standard FZ/T 50012-2006 "Determination of carboxyl-terminated content in polyester titration analysis method".
4. Determination of plastic melting temperature: Determine the melting temperature of the sample with Perkin Elmer DSC-6 analyzer. The flow rate of nitrogen gas is 20 mL/min, and the temperature increase rate is 10° C./min.
5. Determination of biodegradation: Refer to the determination method of ISO014855. Take the $CO_2$ release of the material after 90 days' composting as degradability indicator.

Description of relevant reagents used:
1. Polyether dibasic alcohol containing aromatic nucleus: with the trademark of Simulsol BPPE (simplified as BPPE below), the molecular weight is 660-750 g/mol, $R_1$ and $R_2$ are —$CH_3$, and a+b=7~10;
2. Polyether tetrahydroxy alcohol: with the trademark of Simulsol PTZE (simplified as PTZE below), the molecular weight is 1100-1250 g/mol, $R_3$, $R_4$, $R_5$ and $R_6$ are —$CH_3$, and c+d+e+f=15~20;
3. Isocyanurate-cyclo-polyether-polybasic alcohol: with the trademark of KingSM-I, self-made, $R_{10}$, $R_{11}$ and $R_{12}$ are —$CH_3$, and m+n+k=15
4. Products containing carbonized diimine: with the trademark of Carbodilite E-02 (simplified as E-02 below), produced by Nissin Textile Co. Ltd., the solid content is 40%, the pH value is 9-11, the viscosity at 20° C. is 5~50 mPa·s, and the equivalent weight as carbonized diimine is 445;
5. The other reagents without description are all marketable synthetic products, and the process parameters without description refer to those for conventional process of existing technologies.

Implementation Example 1

Add 330 kg 1,5-pentanediol and 175 kg dimethyl terephthalate into the reaction kettle. With the protection of nitrogen gas, increase the temperature to 185° C. Then add 319 g tetrabutyl titanate. Maintain the temperature inside the reaction kettle at 190° C. Add 161 kg azelaic acid after 4 hours' reaction. Allow it to react for 4 hours at 200° C.

Then increase the temperature to 210° C. After one hour's reaction at low vacuum (90 KPa), add 200 g tetrabutyl titanate. When the temperature reaches 230° C., react for 30 min. Then start to slowly increase the temperature to 245° C. and gradually increase the degree of vacuum to make the pressure inside the kettle reach 1 KPa. Keep the temperature unchanged, and maintain the pressure inside the kettle below 80 Pa. Allow it to react for 3.5 hours to obtain the product.

The relevant indicators of the obtained product are: molecular weight: Mn=38860, Mw=67500, viscosity: 1.18 dL/g, terminated carboxyl: 50 mol/t, melting point: 113.8° C., 90-day degradation rate is calculated as 78% as $CO_2$ emission.

Implementation Example 2

Add 300 kg 1,4-butanediol, 140 kg dimethyl terephthalate and 640 g glycerin into the reaction kettle. With the protection of nitrogen gas, increase the temperature to 170° C. Then add 350 g tetrabutyl titanate. Maintain the temperature inside the reaction kettle at 190° C. Add 210 kg adipic acid after 4 hours' reaction. Allow it to react for 4 hours at 200° C.

Then increase the temperature to 210° C. After 1 h 40 min's reaction at low vacuum (90 KPa), add 200 g tetrabutyl titanate. When the temperature reaches 230° C., react for 30 min. Then start to slowly increase the temperature to 245° C. and gradually increase the degree of vacuum to make the pressure inside the kettle reach 1 KPa. Keep the temperature unchanged, and maintain the pressure inside the kettle below 80 Pa. Allow it to react for 3.5 hours to obtain the product.

The relevant indicators of the obtained product are: molecular weight: Mn=56490, Mw=112850, viscosity: 1.27 dL/g, terminated carboxyl: 75 mol/t, melting point: 124.0° C., 90-day degradation rate is calculated as 79% as $CO_2$ emission.

Implementation Example 3

Add 290 kg isosorbide, 170 kg dimethyl terephthalate and 1200 g trimesic acid into the reaction kettle. With the protection of nitrogen gas, increase the temperature to 180° C. Then add 450 g tetrabutyl titanate. Maintain the temperature inside the reaction kettle at 200° C. Add 170 kg succinic acid after 4.5 hours' reaction. Allow it to react for 4 hours at 210° C. Add 2 kg tri(2-hydroxyethyl) isocyanurate.

Then increase the temperature to 220° C. After 1 hour's reaction at low vacuum (90 KPa), add 200 g tetrabutyl titanate. When the temperature reaches 230° C., react for 30 min. Then start to slowly increase the temperature to 245° C. and gradually increase the degree of vacuum to make the pressure inside the kettle reach 1 KPa. Keep the temperature unchanged, and maintain the pressure inside the kettle below 80 Pa. Allow it to react for 3.5 hours to obtain the product.

The relevant indicators of the obtained product are: molecular weight: Mn=49380, Mw=102170, viscosity: 1.25 dL/g, terminated carboxyl: 64 mol/t, crystallization temperature: 30.0° C., 90-day degradation rate is calculated as 85% as CO2 emission.

Implementation Example 4

Add 1 kg 1,4-butanediol, 0.2 kg glycol, 1 kg p-Phenylenediacetic acid and 400 g PTZE into the reaction kettle. With the protection of nitrogen gas, increase the temperature to 170° C. Add 30 g tetrabutyl titanate. Maintain the temperature inside the reaction kettle at 180° C. Add 1.3 kg azelaic acid after 4 hours' reaction. Allow it to react for 4 hours at 180° C.

Then increase the temperature to 190° C. After 40 min's reaction at low vacuum (around 80 KPa), add 30 g tetrabutyl titanate. Then slowly increase the temperature to 235° C. and gradually increase the degree of vacuum. When the temperature reaches 235° C., allow the pressure inside the kettle to reach 10 KPa. Keep the temperature unchanged, and allow the pressure inside the kettle to drop below 100 Pa. React for 3 hours. Add about 15 g E-02 into the obtained substance. The product is obtained with the processing of anisotropic double screw at 210° C.

The relevant indicators of the obtained product are: molecular weight: Mn=61860, Mw=121100, viscosity: 1.36 dL/g, terminated carboxyl: 87 mol/t, melting point: 108.0° C., 90-day degradation rate is calculated as 81% as $CO_2$ emission.

Implementation Example 5

Add 80 g 1,6-hexanediol, 20 g BPPE product, 35 g p-phenylene diacetic acid, 21 g glutaric acid and 0.24 g pentaerythritol into the flask. With the protection of nitrogen gas, increase the temperature to 180° C. Allow it to react for 4 hours, and then add 60 g tetrabutyl titanate. Add 0.2 g tetrabutyl titanate. Allow it to react for 4 hours' at 180° C.

Then increase the temperature to 220° C. Maintain the low vacuum (around 80 KPa) for about 40 minutes. Slowly increase the temperature to 245° C. and gradually increase the degree of the vacuum. When the temperature drops to 235° C., increase the pressure inside the kettle to 2 KPa. Maintain the temperature, and allow the pressure inside the kettle to drop below 100 Pa. Allow it to react for 2 hours to obtain the product.

The relevant indicators of the obtained product are: molecular weight: Mn=55090, Mw=150420, viscosity: 1.20 dL/g, terminated carboxyl: 30 mol/t, melting point: 107.2° C., 90-day degradation rate is calculated as 89% as $CO_2$ emission.

Implementation Example 6

Add 80 g 1,6-hexanediol, 20 g BPPE product, 35 g p-phenylenediacetic acid, 24 g glutaric acid and 0.24 g pentaerythritol into the flask. With the protection of nitrogen gas, increase the temperature to 180° C. Allow it to react for 4 hours, and then add 60 g dimethyl terephthalate and 0.2 g tetrabutyl titanate. Allow it to react for 4 hours at 180° C.

Then increase the temperature to 220° C. and maintain the low vacuum (around 120 Kpa) for about 40 minutes. Slowly increase the temperature to 245° C. and gradually increase the degree of vacuum. When the temperature drops to 235° C., allow the pressure inside the kettle to reach 2 KPa. Keep the temperature unchanged, and decrease the pressure inside the kettle to below 100 Pa. Allow it to react for 2 hours. Add about 25 g hexamethylene diisocyanate into the obtained substance. The product is obtained with the processing of anisotropic double screw at 210° C.

The relevant indicators of the obtained product are: molecular weight: Mn=46100, Mw=130100, viscosity: 1.19 dL/g, terminated carboxyl: 35 mol/t, melting point: 101.2° C., 90-day degradation rate is calculated as 82% as $CO_2$ emission.

Implementation Example 7

Replace the 20 g BPPE product in the Implementation Example 6 with 35 g KingSM-I, and keep the other conditions unchanged.

The relevant indicators of the obtained product are: molecular weight: Mn=44300, Mw=145300, viscosity: 1.32 dL/g, terminated carboxyl: 45 mol/t, melting point: 109.7° C., 90-day degradation rate is calculated as 79% as $CO_2$ emission.

Implementation Example 8

Add 44 g 1,5-pentanediol, 24 g glutaric acid, 0.5 g 30% (weight ratio) E-02 petroleum ether solution and 16 g PTZE into the flask. With the protection of nitrogen gas, increase the temperature to 170° C. Add 0.2 g tetrabutyl titanate, and maintain the temperature inside the reaction kettle at 200° C. Allow it to react for 4 hours, and then add 56 g hydracrylic acid. Allow it to react for 2 hours at 200° C.

Then increase the temperature to 210° C. After the reaction at low vacuum around 120 KPa for 40 min, add 0.2 g tetrabutyl titanate. Allow it to react for 30 min, and slowly increase the temperature to 235° C. to increase the pressure inside the kettle to 3 KPa. Keep the temperature unchanged, and decrease the pressure inside the kettle below 100 Pa. Allow it to react for 2 hours. Add about 35 g toluene diisocyanate blocked by butanone oxime into the obtained substance. The product is obtained with the processing of anisotropic double screw at 210° C.

The relevant indicators of the obtained product are: molecular weight: Mn=95400, Mw=217200, viscosity: 1.59 dL/g, terminated carboxyl: 42 mol/t, melting point: 136.2° C., 90-day degradation rate is calculated as 71% as $CO_2$ emission.

Implementation Example 9

In the implementation example, the prepared biodegradable polyester contains no Component B.

Add 300 kg 1,4-butanediol, 100 kg dimethyl terephthalate and 640 g glycerin into the reaction kettle. With the protection of nitrogen gas, increase the temperature to 170° C. Add 350 g tetrabutyl titanate, and maintain the temperature in the reaction kettle at 190° C. After 4 hours' reaction, add 210 g azelaic acid and 100 kg salicylic acid. Allow it to react for 4 hours at 200° C.

Then increase the temperature to 210° C. After 1 h 40 min's reaction at low vacuum (90 KPa), add 200 g tetrabutyl titanate. When the temperature reaches 230° C. Allow it to react for 30 min. Then start to slowly increase the temperature to 245° C. and gradually increase the degree of vacuum until the pressure inside the kettle reaches 1 KPa. Keep the temperature unchanged, and maintain the pressure inside the kettle below 80 Pa. Allow it to react for 3.5 hours to obtain the product.

The relevant indicators of the obtained product are: molecular weight: Mn=55490, Mw=103250, viscosity: 1.29 dL/g, terminated carboxyl: 75 mol/t, melting point: 134.0° C., 90-day degradation rate is calculated as 77% as $CO_2$ emission.

Implementation Example 10

The reaction conditions and the addition quantities of reactants are same as those of Implementation Example 8. Shorten the polycondensation time to 3.3 hours to obtain the product with slightly low molecular weight.

The relevant indicators of the obtained product are: molecular weight: Mn=46270, Mw=88960, viscosity: 1.08 dL/g, terminated carboxyl: 127.2 mol/t, melting point: 106.5° C., 90-day degradation rate is calculated as 93% as $CO_2$ emission.

Implementation Example 11

Add 44 g 1,5-pentanediol, 37 g dimethyl terephthalate, 0.5 g 30% (weight ratio) E-02 petroleum ether solution and 16 g PTZE into the flask. With the protection of nitrogen gas, increase the temperature to 170° C. Add 0.2 g tetrabutyl titanate. Maintain the temperature inside the reaction kettle at 200° C. Allow it to react for 4 hours. Then add 32 g glycolic acid. Allow it to react for 2 hours at 200° C.

Then increase the temperature to 210° C. After 40 min's reaction at low vacuum (around 80 KPa), add 0.2 g tetrabutyl titanate. Allow it to react for 30 minutes. Slowly increase the temperature to 235° C. and allow the pressure inside the kettle to reach 5-3 KPa. Keep the temperature unchanged, and allow the pressure inside the kettle drop below 100 Pa. Allow it to react for 2 hours to obtain the product.

The relevant indicators of the obtained product are: molecular weight: Mn=55300, Mw=120100, viscosity: 1.23 dL/g, terminated carboxyl: 82 mol/t, melting point: 136.2° C., 90-day degradation rate is calculated as 74% as $CO_2$ emission.

Implementation Example 12

Add 10 kg isosorbide, 8.5 kg p-phenylene diacetic acid, 80 g dipentaerythritol and 30 g tetrabutyl titanate into the reaction kettle. Allow it to react for 5.5 hours at 220° C. Add 5 kg adipic acid and 4 kg azelaic acid. Allow it to react for 3 hours at 175° C. Add about 200 g E-02.

Increase the temperature to 190° C. Maintain the low vacuum (around 80 KPa) for about 40 min. Add 30 g tetrabutyl titanate. Allow it to react for 30 minutes. Slowly increase the temperature to 245° C. to allow the pressure inside the kettle to reach 4 KPa. Keep the temperature unchanged, and maintain the pressure inside the kettle below 100 Pa. Allow it to react for 3 hours to obtain the product.

The relevant indicators of the obtained product are: molecular weight: Mn=49100, Mw=112400, viscosity: 1.28 dL/g, terminated carboxyl: 82 mol/t, melting point: 118.0° C., 90-day degradation rate is calculated as 89% as $CO_2$ emission.

Implementation Example 13

Add 189 g 1,5-pentanediol, 184 g azelaic acid dimethyl ester and 175 kg dimethyl terephthalate into the reaction kettle. With the protection of nitrogen gas, increase the temperature to 185° C. Add 319 g tetrabutyl titanate. Maintain the temperature inside the reaction kettle at 190° C. Allow it to react for 4 hours.

Then increase the temperature to 210° C. After 1 hour's reaction at low vacuum (90 KPa), add 200 g tetrabutyl titanate. After the temperature reaches 230° C. Allow it to react for 30 minutes. Slowly increase the temperature to 245° C. and gradually increase the degree of vacuum to allow the pressure inside the kettle to reach 1 KPa. Keep the temperature unchanged, and allow the pressure inside the kettle to drop below 80 Pa. Allow it to react for 3.5 hours to obtain the product.

The relevant indicators of the obtained product are: molecular weight: Mn=38000, Mw=69300, viscosity: 1.20 dL/g, terminated carboxyl: 46 mol/t, melting point: 112.5° C., 90-day degradation rate is calculated as 76% as $CO_2$ emission.

Implementation Example 14

Add 240 g 1,4-butanediol, 140 kg dimethyl terephthalate, 250 kg adipic acid dimethyl ester and 640 g glycerin into the reaction kettle. With the protection of nitrogen gas, increase the temperature to 170° C. Add 350 g tetrabutyl titanate. Maintain the temperature inside the reaction kettle at 190° C. Allow it to react for 4 hours.

Then increase the temperature to 210° C. After 1 h 40 min's reaction at low vacuum (90 KPa), add 200 g tetrabutyl titanate. After the temperature reaches 230° C. Allow it to react for 30 minutes. Slowly increase the temperature to 245° C. and gradually increase the degree of vacuum so the pressure inside the kettle reaches 1 KPa. Keep the temperature unchanged, and allow the pressure inside the kettle to drop below 80 Pa. Allow it to react for 3.5 hours to obtain the product.

The relevant indicators of the obtained product are: molecular weight: Mn=57000, Mw=122000, viscosity: 1.25 dL/g, terminated carboxyl: 55 mol/t, melting point: 123.0° C., 90-day degradation rate is calculated as 81% as $CO_2$ emission.

Implementation Example 15

Add 290 g isosorbide, 170 kg dimethyl terephthalate, 210 kg dimethyl succinate and 1000 g 1,2,4,5-benzene tetracarboxylic anhydride into the reaction kettle. With the protection of nitrogen gas, increase the temperature to 180° C. Add 450 g tetrabutyl titanate. Maintain the temperature inside the reaction kettle at 200° C. After 4.5 hours' reaction, add 2 kg tri(2-hydroxyethyl) isocyanurate.

Then increase the temperature to 220° C. After 1 hour's reaction at low vacuum (90 KPa), add 200 g tetrabutyl titanate. After the temperature reaches 230° C. Allow it to react for 30 minutes. Slowly increase the temperature to 245° C. and gradually increase the degree of vacuum to allow the pressure inside the kettle to reach 1 KPa. Keep the temperature unchanged, and allow the pressure inside the kettle to drop below 80 Pa. Allow it to react for 3.5 hours to obtain the product.

The relevant indicators of the obtained product are: molecular weight: Mn=48300, Mw=112000, viscosity: 1.23 dL/g, terminated carboxyl: 49 mol/t, crystallization temperature: 31.0° C., 90-day degradation rate is calculated as 87% as $CO_2$ emission.

Implementation Example 16

Add 1 kg 1,4-butanediol, 0.2 kg glycol, 1.3 kg azelaic acid, 1 kg p-phenylenediacetic acid and 400 g PTZE into the reaction kettle. With the protection of nitrogen gas, increase the temperature to 170° C. Add 30 g tetrabutyl titanate. Maintain the temperature inside the reaction kettle at 180° C. Allow it to react for 4 hours.

Then increase the temperature to 190° C. After 40 min's reaction at low vacuum (around 80 KPa), add 30 g tetrabutyl titanate. Then slowly increase the temperature to 235° C. and gradually increase the degree of vacuum. When the temperature reaches 235° C., allow the pressure inside the kettle to reach 10 KPa. Keep the temperature unchanged, and allow the pressure inside the kettle to drop below 100 Pa. Allow it to react for 3 hours. Add about 15 g E-02 into the obtained substance. The product is obtained with the processing of anisotropic double screw at 210° C.

The relevant indicators of the obtained product are: molecular weight: Mn=63000, Mw=128000, viscosity: 1.35 dL/g, terminated carboxyl: 69 mol/t, melting point: 110.0° C., 90-day degradation rate is calculated as 83% as $CO_2$ emission.

Implementation Example 17

Add 80 g 1,6-hexanediol, 20 g BPPE product, 35 g p-phenylenediacetic acid, 21 g succinic acid and 0.21 g citric acid into the flask. With the protection of nitrogen gas, increase the temperature to 180° C. Allow it to react for 4 hours, and then add 60 g dimethyl terephthalate and 0.2 g tetrabutyl titanate. Allow it to react for 4 hours at 180° C.

Then increase the temperature to 220° C. and maintain the low vacuum (around 80 Kpa) for about 40 minutes. Slowly increase the temperature to 245° C. and gradually increase the degree of vacuum. When the temperature drops to 235° C., allow the pressure inside the kettle to reach 2 KPa. Keep the temperature unchanged, and allow the pressure inside the kettle drop below 100 Pa. Allow it to react for 2 hours to obtain the product.

The relevant indicators of the obtained product are: molecular weight: Mn=51030, Mw=120500, viscosity: 1.22 dL/g, terminated carboxyl: 40 mol/t, melting point: 110.0° C., 90-day degradation rate is calculated as 92% as $CO_2$ emission.

Implementation Example 18

Add 80 g 1,5-pentanediol, 20 g BPPE product, 35 g p-phenylenediacetic acid, 21 g succinic acid and 0.24 g pentaerythritol into the flask. With the protection of nitrogen gas, increase the temperature to 180° C. Allow it to react for 4 hours, and then add 60 g dimethyl terephthalate and 0.2 g tetrabutyl titanate. Allow it to react for 4 hours at 180° C.

Then increase the temperature to 220° C. and maintain the low vacuum (around 80 KPa) for about 40 minutes. Slowly increase the temperature to 245° C. and gradually increase the degree of vacuum. When the temperature drops to 235° C., allow the pressure inside the kettle to reach 2 KPa. Keep the temperature unchanged, and maintain the pressure inside the kettle below 100 Pa. React for 2 hours. Add about 25 g hexamethylene diisocyanate into the obtained substance. The product is obtained with the processing of anisotropic double screw at 210° C.

The relevant indicators of the obtained product are: molecular weight: Mn=53100, Mw=120500, viscosity: 1.21 dL/g, terminated carboxyl: 43 mol/t, melting point: 109.0° C., 90-day degradation rate is calculated as 85% as $CO_2$ emission.

Implementation Example 19

Add 40 g 1,4-butanediol, 21 g succinic acid, 0.5 g 30% (weight ratio) E-02 petroleum ether solution and 16 g PTZE into the flask. With the protection of nitrogen gas, increase the temperature to 170° C. Add 0.2 g tetrabutyl titanate. Maintain the temperature inside the reaction kettle at 200° C. Allow it to react for 4 hours. Then add 56 g glycolic acid. Allow it to react for 2 hours at 200° C.

Then increase the temperature to 210° C. After 40 min's reaction at low vacuum (around 80 KPa), add 0.2 g tetrabutyl titanate. Allow it to react for 30 minutes. Slowly increase the temperature to 235° C. and allow the pressure inside the kettle to reach 3 KPa. Keep the temperature unchanged, and allow the pressure inside the kettle to drop below 100 Pa. React for 2 hours. Add about 35 g toluene diisocyanate blocked by butanone oxime into the obtained substance. The product is obtained with the processing of anisotropic double screw at 210° C.

The relevant indicators of the obtained product are: molecular weight: Mn=90200, Mw=187200, viscosity: 1.45 dL/g, terminated carboxyl: 46 mol/t, melting point: 140.2° C., 90-day degradation rate is calculated as 75% as $CO_2$ emission.

Implementation Example 20

Add 250 g 1,4-butanediol, 100 kg dimethyl terephthalate, 240 kg sebacic aciddimethyl ester and 640 g glycerin into the reaction kettle. With the protection of nitrogen gas, increase the temperature to 170° C. Add 350 g tetrabutyl titanate. Maintain the temperature inside the reaction kettle at 190° C. Allow it to react for 4 hours. Then add 100 g salicylic acid. Allow it to react for 4 hours at 200° C.

Then increase the temperature to 210° C. After 1 h 40 min's reaction at low vacuum (90 KPa), add 200 g tetrabutyl titanate. After the temperature reaches 230° C., allow it to react for 30 minutes. Slowly increase the temperature to 245° C. and gradually increase the degree of vacuum to allow the pressure inside the kettle to reach 1 KPa. Keep the temperature unchanged, and allow the pressure inside the kettle to drop below 80 Pa. Allow it to react for 3.5 hours to obtain the product.

The relevant indicators of the obtained product are: molecular weight: Mn=51300, Mw=93500, viscosity: 1.25 dL/g, terminated carboxyl: 66 mol/t, melting point: 129.0° C., 90-day degradation rate is calculated as 71% as $CO_2$ emission.

Implementation Example 21

Add 44 g 1,5-pentanediol, 35 g terephthalic acid, 0.5 g 30% (weight ratio) E-02 petroleum ether solution and 16 g PTZE into the flask. With the protection of nitrogen gas, increase the temperature to 170° C. Add 0.2 g tetrabutyl titanate. Maintain the temperature inside the reaction kettle at 220° C. Allow it to react for 4 hours. Then add 32 g glycolic acid. Allow it to react for 2 hours at 220° C.

Then increase the temperature to 230° C. After 40 min's reaction at low vacuum (around 80 KPa), add 0.2 g tetrabutyl titanate. Allow it to react for 30 minutes. Slowly increase the temperature to 235° C. and allow the pressure inside the kettle to reach 5-3 KPa. Keep the temperature unchanged, and allow the pressure inside the kettle to drop below 100 Pa. React for 2 hours to obtain the product.

The relevant indicators of the obtained product are: molecular weight: Mn=56700, Mw=11200, viscosity: 1.24 dL/g, terminated carboxyl: 74 mol/t, melting point: 126.2° C., 90-day degradation rate is calculated as 76% as $CO_2$ emission.

Implementation Example 22

Add 10 kg isosorbide, 8.5 kg p-Phenylenediacetic acid, 60 kg 1,2,4,5-benzene tetracarboxylic anhydride, 5 kg adipic acid, 4 kg azelaic acid and 30 g tetrabutyl titanate into the reaction kettle. Allow it to react for 5 hours at 230° C. Add about 200 g E-02.

Maintain the low vacuum (around 80 KPa) for about 40 minutes. Add 30 g tetrabutyl titanate. Allow it to react for 30 minutes. Slowly increase the temperature to 245° C. and allow the pressure inside the kettle to reach 4 KPa. Keep the temperature unchanged and allow the pressure inside the kettle to drop to below 100 Pa. Allow it to react for 3 hours to obtain the product.

The relevant indicators of the obtained product are: molecular weight: Mn=54100, Mw=12300, viscosity: 1.31 dL/g, terminated carboxyl: 71 mol/t, crystallization temperature: 116.0° C., 90-day degradation rate is calculated as 85% as $CO_2$ emission.

Implementation Example 23

Add 300 kg 1,4-butanediol, 130 kg dimethyl terephthalate, 10 kgm-phthalic aciddimethyl ester, 210 kg adipic aciddimethyl ester and 640 g glycerin into the reaction kettle. With the protection of nitrogen gas, increase the temperature to 170° C. Add 350 g tetrabutyl titanate. Maintain the temperature inside the reaction kettle at 190° C. Allow it to react for 4 hours.

Then increase the temperature to 210° C. After 1 h 40 min's reaction at low vacuum (90 KPa), add 200 g tetrabutyl titanate. After the temperature reaches 230° C., allow it to react for 30 minutes. Slowly increase the temperature to 245° C. and gradually increase the degree of vacuum to allow the pressure inside the kettle to reach 1 KPa. Keep the temperature unchanged, and allow the pressure inside the kettle to drop to below 80 Pa. Allow it to react for 3.5 hours to obtain the product.

The relevant indicators of the obtained product are: molecular weight: Mn=61300, Mw=104000, viscosity: 1.23 dL/g, terminated carboxyl: 55 mol/t, melting point: 132.0° C., 90-day degradation rate is calculated as 72% as $CO_2$ emission.

Implementation Example 24

Add 1 kg 1,4-butanediol, 0.2 kg 1,3-propanediol, 1 kg p-phenylenediacetic acid and 400 g PTZE into the reaction kettle. With the protection of nitrogen gas, increase the temperature to 170° C. Add 30 g tetrabutyl titanate. Maintain the temperature inside the reaction kettle at 180° C. Allow it to react for 4 hours. Then add 1.7 kg sebacic acid. Allow it to react for 4 hours at 180° C.

Then increase the temperature to 190° C. After 40 min's reaction at low vacuum (around 80 KPa), add 30 g tetrabutyl titanate. Slowly increase the temperature to 235° C. and gradually increase the degree of vacuum. When the temperature reaches 235° C., allow the pressure inside the kettle to reach 10 KPa. Keep the temperature unchanged, and allow the pressure inside the kettle to drop to below 100 Pa. Allow it to react for 3 hours. Add about 15 g E-02 into the obtained substance. The product is obtained with the processing of anisotropic double screw at 210° C.

The relevant indicators of the obtained product are: molecular weight: Mn=52700, Mw=116800, viscosity: 1.31 dL/g, terminated carboxyl: 50 mol/t, melting point: 118.0° C., 90-day degradation rate is calculated as 76% as $CO_2$ emission.

Implementation Example 25

Add 1 kg 1,4-butanediol, 0.2 kg glycol, 1 kg p-phenylenediacetic acid, 400 g PTZE and 20 g citric acid into the reaction kettle. With the protection of nitrogen gas, increase the temperature to 170° C. Add 30 g tetrabutyl titanate. Maintain the temperature inside the reaction kettle at 180° C. Allow it to react for 4 hours. Then add 1.6 kg sebacic acid. Allow it to react for 4 hours at 180° C.

Then increase the temperature to 190° C. After 40 min's reaction at low vacuum (around 80 KPa), add 30 g tetrabutyl titanate. Slowly increase the temperature to 235° C. and gradually increase the degree of vacuum. When the temperature reaches 235° C., allow the pressure inside the kettle to reach 10 KPa. Keep the temperature unchanged, and allow the pressure inside the kettle to drop to below 100 Pa. Allow it to react for 3 hours. Add about 15 g E-02 into the obtained substance. The product is obtained with the processing of anisotropic double screw at 210° C.

The relevant indicators of the obtained product are: molecular weight: Mn=61860, Mw=121100, viscosity: 1.36 dL/g, terminated carboxyl: 87 mol/t, melting point: 108.0° C., 90-day degradation rate is calculated as 81% as $CO_2$ emission.

Implementation Example 26

Add 1 kg 1,4-butanediol, 0.2 kg glycol, 0.8 kg p-phenylenediacetic acid, 0.2 kg m-phthalic acid and 400 g PTZE into the reaction kettle. With the protection of nitrogen gas, increase the temperature to 170° C. Add 30 g tetrabutyl titanate. Maintain the temperature inside the reaction kettle at 180° C. Allow it to react for 4 hours. Then add 1.5 kg sebacic acid. Allow it to react for 4 hours at 180° C.

Then increase the temperature to 190° C. After 40 min's reaction at low vacuum (around 80 KPa), add 30 g tetrabutyl titanate. Slowly increase the temperature to 235° C. and gradually increase the degree of vacuum. When the temperature reaches 235° C., allow the pressure inside the kettle to reach 10 KPa. Keep the temperature unchanged, and allow the pressure inside the kettle to drop to below 100 Pa. Allow it to react for 3 hours. Add about 15 g E-02 into the obtained substance. The product is obtained with the processing of anisotropic double screw at 210° C.

The relevant indicators of the obtained product are: molecular weight: Mn=65700, Mw=103200, viscosity: 1.31 dL/g, terminated carboxyl: 90 mol/t, melting point: 112.0° C., 90-day degradation rate is calculated as 78% as $CO_2$ emission.

Implementation Example 27

Add 1 kg 1,4-butanediol, 0.2 kg glycol, 0.8 kg p-phenylenediacetic acid, 0.2 kg m-phthalic acid and 400 g PTZE into the reaction kettle. With the protection of nitrogen gas, increase the temperature to 170° C. Add 30 g tetrabutyl titanate. Maintain the temperature inside the reaction kettle at 180° C. Allow it to react for 4 hours. Then add 1.0 kg sebacic acid and 0.5 kg succinic acid. Allow it to react for 4 hours at 180° C.

Then increase the temperature to 190° C. After 40 min's reaction at low vacuum (around 80 KPa), add 30 g tetrabutyl titanate. Slowly increase the temperature to 235° C. and gradually increase the degree of vacuum. When the temperature reaches 235° C., allow the pressure inside the kettle to reach 10 KPa. Keep the temperature unchanged, and allow the pressure inside the kettle to drop to below 100 Pa. Allow it to react for 3 hours. Add about 15 g E-02 into the obtained substance. The product is obtained with the processing of anisotropic double screw at 210° C.

The relevant indicators of the obtained product are: molecular weight: Mn=55640, Mw=130200, viscosity: 1.41 dL/g, terminated carboxyl: 67 mol/t, melting point: 114.0° C., 90-day degradation rate is calculated as 85% as $CO_2$ emission.

Comparison Example 1

Add 80 g 1,6-hexanediol, 40 g BPPE product, 70 g p-phenylenediacetic acid, 24 g glutaric acid and 0.24 g pentaerythritol into the flask. With the protection of nitrogen gas, increase the temperature to 180° C. Allow it to react for 4 hours, and then add 60 g dimethyl terephthalate and 0.2 g tetrabutyl titanate. Allow it to react for 4 hours at 180° C.

Then increase the temperature to 220° C. and maintain the low vacuum (around 80 Kpa) for about 40 minutes. Slowly increase the temperature to 245° C. and gradually increase the degree of vacuum. When the temperature drops to 235° C., make the pressure inside the kettle reach 2 KPa. Keep the temperature unchanged, and allow the pressure inside the kettle to drop below 100 Pa. React for 2 hours to obtain the product. Add about 25 g hexamethylene diisocyanate into the obtained substance. The product is obtained with the processing of anisotropic double screw at 210° C.

The relevant indicators of the obtained product are: molecular weight: Mn=46100, Mw=130100, viscosity: 1.19 dL/g, terminated carboxyl: 35 mol/t, melting point: 121.2° C., 90-day degradation rate is calculated as 59% as $CO_2$ emission.

Comparison Example 2

Add 135 kg 1,4-butanediol, 85.3 g m-phthalic acid and 59 g succinic acid into the four-neck flask. With the protection of nitrogen gas, increase the temperature to 170° C. Add 0.07 g tetrabutyl titanate. Maintain the temperature inside the reaction kettle at 210° C. Allow it to react for 4 hours.

Then increase the temperature to 220° C. After 40 min's reaction at low vacuum (around 80 KPa), add 0.07 g tetrabutyl titanate. Slowly increase the temperature to 235° C. and gradually increase the degree of vacuum. When the temperature reaches 235° C., allow the pressure inside the kettle to reach 10 KPa. Keep the temperature unchanged, and allow the pressure inside the kettle to drop to below 100 Pa. Allow it to react for 3 hours.

The relevant indicators of the obtained product are: molecular weight: Mn=22000, Mw=61000, viscosity: 1.14 dL/g, terminated carboxyl: 50 mol/t, melting point: 121.0° C., 90-day degradation rate is calculated as 30% as $CO_2$ emission.

Comparison Example 3

Add 135 g 1,4-butanediol, 66.8 g terephthalic acid, 35.5 g succinic acid, 36.5 g adipic acid and 0.7 g tetrabutyl titanate into the four-neck flask. With the protection of nitrogen gas, increase the temperature to 200° C. Make it react for 2 hours.

Then increase the temperature to 220° C. After 40 min's reaction at low vacuum (around 80 KPa), add 0.07 g tetrabutyl titanate. Slowly increase the temperature to 245° C. and gradually increase the degree of vacuum. When the temperature reaches 245° C., allow the pressure inside the kettle to reach 10 KPa. Keep the temperature unchanged, and allow the pressure inside the kettle to drop to below 100 Pa. Allow it to react for 3 hours.

The relevant indicators of the obtained product are: molecular weight: Mn=15000, Mw=43000, viscosity: 0.9 dL/g, terminated carboxyl: 50 mol/t, melting point: 1081.0° C., 90-day degradation rate is calculated as 42% as $CO_2$ emission.

Comparison Example 4

Add 135 g 1,4-butanediol, 66.8 g terephthalic acid, 70 g succinic acid and 0.7 g tetrabutyl titanate into the four-neck flask. With the protection of nitrogen gas, increase the temperature to 200° C. Make it react for 2 hours.

Then increase the temperature to 220° C. After 40 min's reaction at low vacuum (around 80 KPa), add 0.07 g tetrabutyl titanate. Slowly increase the temperature to 245° C. and gradually increase the degree of vacuum. When the temperature reaches 245° C., allow the pressure inside the kettle to reach 10 KPa. Keep the temperature unchanged, and allow the pressure inside the kettle to drop to below 100 Pa. Allow it to react for 3 hours.

The relevant indicators of the obtained product are: molecular weight: Mn=18000, Mw=52000, viscosity: 1.0 dL/g, terminated carboxyl: 65 mol/t, melting point: 92.0° C., 90-day degradation rate is calculated as 21% as $CO_2$ emission.

Comparison Example 5

Add 6.3 g 1,4-butanediol, 2.95 g succinic acid, 3.65 g adipic acid and 0.1 g tetrabutyl titanate into the four-neck flask. With the protection of nitrogen gas, increase the temperature to 205° C. Allow it to react for 2 hours. Then add 78.8 g dimethyl terephthalate, 126 g butanediol and 6.2 g glycol. Allow it to react for 2 hours at 205° C. until there is methanol.

Then increase the temperature to 220° C. After 40 min's reaction at low vacuum (around 80 KPa), add 0.07 g tetrabutyl titanate. Slowly increase the temperature to 245° C. and gradually increase the degree of vacuum. When the temperature reaches 245° C., allow the pressure inside the kettle to reach 10 KPa. Keep the temperature unchanged, and allow the pressure inside the kettle to drop to below 100 Pa. Allow it to react for 3 hours.

The relevant indicators of the obtained product are: molecular weight: Mn=47000, Mw=230000, viscosity: 1.6 dL/g, terminated carboxyl: 35 mol/t, melting point: 92.0° C., 90-day degradation rate is calculated as 65% as $CO_2$ emission.

It is shown by the results of the above implementation examples and comparison examples that, the biodegradable polyesters obtained by this invention have obvious biodegradable property. The processes are easy for operation, and the product performance is excellent. According to the comparison with the comparison examples, it is also shown that, when the ratio of added dibasic acid is relatively high in the synthesis system in Component A12, although the biodegradable polyesters satisfying the requirements of molecular weight and viscosity could be obtained, there will be major negative impacts on the biodegradability of the polyesters.

What is claimed is:

1. A biodegradable polyester having a number-average molecular weight of 6000-135000 g/mol, a molecular weight distribution of from 1.2-6.5 and a crystallization temperature range of from 15° C.-105° C., comprising 94-99.9 mole percent Component A and 0.1-6 mole percent Component B, wherein
   Component A comprises Component A1 and Component A2 having a molar ratio of 0.35-1.6:1;
   Component A1 comprises 20-100 mole percent Component A11 and 0-80 mole percent Component A12;
   Component A11 is selected from the group consisting of aliphatic dibasic acid, cyclic aliphatic dibasic acid, esterified derivatives of aliphatic dibasic acid, esterified derivatives of cyclic aliphatic dibasic acid, and mixtures thereof;
   Component A12 is selected from the group consisting of an aromatic dibasic acid, an ester of an aromatic dibasic acid, and mixtures thereof;
   Component A2 comprises 80-99.9 mole percent Component A21 and 0.1-20 mole percent Component A22;
   A21 comprises at least one of the following substances: an aliphatic dibasic alcohol with a carbon atom number of $C_2$-$C_8$, a cyclic aliphatic dibasic alcohol or polycyclic aliphatic dibasic alcohol with a carbon atom number of $C_5$-$C_{16}$, an aliphatic polyether dibasic alcohol, or a hydroxyl aliphatic acid;
   A22 comprises at least one of the following substances: a dibasic alcohol containing aromatic nucleus or a polyether dibasic alcohol containing an aromatic nucleus or a hydroxyl organic acid containing an aromatic nucleus with a carbon atom number of $C_8$-$C_{18}$;
   Component B is Component B2;
   Component B2 is selected from the group consisting of an isocyanurate cyclic polybasic alcohol, an isocyanate polyether polybasic alcohol, and mixtures thereof, wherein the isocyanurate cyclic polybasic alcohol and isocyanate polyether polybasic alcohol has the molecular structure as shown in Formula III:

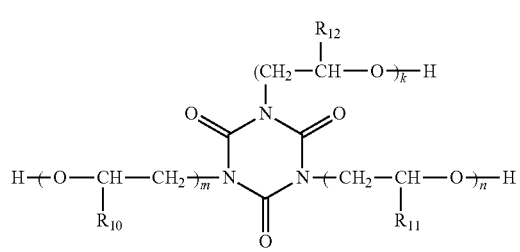

(III)

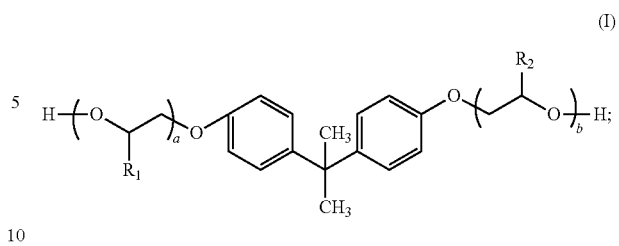

(I)

in which, $R_{10}$, $R_{11}$ and $R_{12}$ could be same or different, which are all —H, —$CH_3$ or —$CH_2CH_3$; m, n and k are numerals selected from any of the positive numbers satisfying the condition of m+n+k equals from 3 to about 30; and wherein the biodegradable polyester is biodegradable.

2. The biodegradable polyester of claim 1, wherein the aliphatic dibasic acid, cyclic aliphatic dibasic acid, esterified derivatives of aliphatic dibasic acid, esterified derivatives of cyclic aliphatic dibasic acid, and mixtures thereof of Component A11 are dibasic acids or their esters with carbon atom number of $C_4$-$C_{18}$.

3. The biodegradable polyester of claim 1, wherein the aliphatic dibasic alcohol in Component A21 is selected from the group consisting of glycol, 1,2-propanediol, 1,3-propanediol, 1,2-butanediol, 1,4-butanediol, 1,5-pentanediol, 2,2-dimethyl-1,3-propanediol, 2-ethyl-2-tert-butyl-1,3-propanediol, 2,2,4-trimethyl-1,6-hexanediol, and mixtures thereof; and wherein the cyclic aliphatic dibasic alcohol in Component A21 is selected from the group consisting of cyclopentanediol, 1,4-cyclo-hexanediol, 1,2-cyclo-hexanedimethanol, 1,3-cyclo-hexanedimethanol, 1,4-cyclo-hexanedimethanol, isosorbide, and mixtures thereof.

4. The biodegradable polyester of claim 1, wherein the cyclic aliphatic dibasic alcohol in Component A21 is isosorbide or its derivative.

5. The biodegradable polyester of claim 1, wherein the aliphatic polyether dibasic alcohol in Component A21 is selected from the group consisting of ethylene oxide dimer, ethylene oxide trimer, polyethylene oxide, Poly(tetramethylene ether glycol), ethylene oxide-propylene oxide copolymer with the molecular weight between 25-12000 g/mol, and mixtures thereof.

6. The biodegradable polyester of claim 1, wherein the hydroxyl aliphatic acid in Component A21 is selected from the group consisting of glycolic acid, α-hydracrylic acid, β-malic acid, β-hydroxybutyric acid, hydroxy-butanedioic acid, 5-hydroxy-valeric acid, 3-hydroxy-hexanoic acid, 5-hydroxy-hexanoic acid, 6-hydroxy-hexanoic acid, 7-hydroxy-heptanoic acid, 3,5-dihydroxy-heptanoic acid, hydroxy-octanoic acid, 5-hydroxy-decanoic acid, 5-hydroxy-dodecanoic acid, 9,10,16-trihydroxy-hexadecanoic acid, 3,4-dihydroxy-cinnamic acid, p-hydroxy-cinnamic acid, agaric acid, their polymers, and mixtures thereof.

7. The biodegradable polyester of claim 1, wherein the dibasic alcohol containing aromatic nucleus and the polyether dibasic alcohol containing an aromatic nucleus in Component A22 have the molecular structure as shown in Formula 1:

in Formula 1, $R_1$ is —H, —$CH_3$ or —$C_2H_5$; $R_2$ is —H, —$CH_3$ or —$C_2H_5$, and a and b are both numerals selected from any of the positive numbers satisfying the condition of a+b equals from 2 to about 30.

8. The biodegradable polyester of claim 1, wherein the hydroxy organic acid containing aromatic nucleus in Component A22 is selected from the group consisting of o-hydroxybenzoic acid, p-hydroxybenzoic acid, 2,4-dihydroxybenzoic acid, 4-hydroxy phthalate and its derivatives, 4-hydroxy-o-phthalic anhydride, the polymer of the above mentioned organic acids, and mixtures thereof.

9. A biodegradable polyester having a number-average molecular weight of 6000-135000 g/mol, a molecular weight distribution of from 1.2-6.5 and a crystallization temperature range of from 15° C.-105° C., comprising 94-99.9 mole percent Component A and 0.1-6 mole percent Component B, wherein Component A comprises Component A1 and Component A2 having a molar ratio of 0.35-1.6:1;

Component A1 comprises 20-100 mole percent Component A11 and 0-80 mole percent Component A12;

Component A11 is selected from the group consisting of aliphatic dibasic acid, cyclic aliphatic dibasic acid, esterified derivatives of aliphatic dibasic acid, esterified derivatives of cyclic aliphatic dibasic acid, and mixtures thereof;

Component A12 is selected from the group consisting of an aromatic dibasic acid, an ester of an aromatic dibasic acid, and mixtures thereof;

Component A2 comprises 80-99.9 mole percent Component A21 and 0.1-20 mole percent Component A22;

A21 comprises at least one of the following substances: an aliphatic dibasic alcohol with a carbon atom number of $C_2$-$C_8$, a cyclic aliphatic dibasic alcohol or polycyclic aliphatic dibasic alcohol with a carbon atom number of $C_5$-$C_{16}$, an aliphatic polyether dibasic alcohol, or a hydroxyl aliphatic acid;

A22 comprises at least one of the following substances: a dibasic alcohol containing aromatic nucleus or a polyether dibasic alcohol containing an aromatic nucleus or a hydroxyl organic acid containing an aromatic nucleus with a carbon atom number of $C_8$-$C_{18}$;

Component B is Component B3;

Component B3 is selected from the group consisting of carbonized diimine compounds, wherein the carbonized diimine compound is carbonized diimine monomer, poly carbonized diimine or the mixture made up of two or more kinds of carbonized diimine compounds containing 1-30 carbonized diimine groups in their molecular structure with the molecular weight of 40-30000 g/mol at any ratio;

wherein the biodegradable polyester is biodegradable.

10. A method for preparing the biodegradable polyester of claim 1, comprising an esterification phase, an ester exchange phase, and a condensation polymerization phase; wherein Component B is added at any reaction phase or before or after any reaction phase to prepare the biodegradable polyester; wherein Component B is added once or several times before, during, or after one or more reaction phases.

11. A biodegradable polyester having a number-average molecular weight of 6000-135000 g/mol, a molecular weight distribution of 1.2-6.5 and a crystallization temperature range of from 15° C.-105° C., comprising 94-99.9 mole percent of Component A and 0.1-6 mole percent of Component B; wherein Component A comprises Component A1 and Component A2 at a molar ratio of 0.35-1.6:1;
Component A1 comprises 20-100 mole percent of Component A11 and 0-80 mole percent of Component A12;
Component A11 is selected from the group consisting of aliphatic dibasic acid, cyclic aliphatic dibasic acid, esterified derivatives of aliphatic dibasic acid, esterified derivatives of cyclic aliphatic dibasic acid, and mixtures thereof;
Component A12 is selected from the group consisting of an aromatic dibasic acid, an ester of aromatic dibasic acid, and mixtures thereof;
Component A2 comprises 80-99.9 mole percent Component A21 and 0.1-20 mole percent Component A22;
A21 comprises at least one of the following substances: an aliphatic dibasic alcohol with a carbon atom number of $C_2$-$C_8$, a cyclic aliphatic dibasic alcohol or polycyclic aliphatic dibasic alcohol with a carbon atom number of $C_5$-$C_{16}$, an aliphatic polyether dibasic alcohol, and a hydroxyl aliphatic acid;
A22 comprises at least one of the following substances: a dibasic alcohol containing aromatic nucleus or a polyether dibasic alcohol containing an aromatic nucleus or a hydroxyl organic acid containing an aromatic nucleus with a carbon atom number of $C_8$-$C_{18}$;
Component B is selected from the group consisting of Component B2, Component B3, and mixtures thereof at any mass ratio;
Component B2 is selected from the group consisting of isocyanurate cyclic polybasic alcohol or isocyanate polyether polybasic alcohol, and mixtures thereof, wherein the isocyanurate cyclic polybasic alcohol and isocyanate polyether polybasic alcohol has the molecular structure as shown in Formula III:

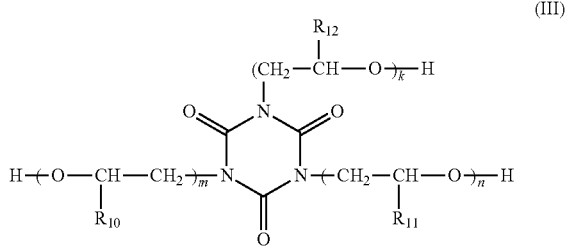

(III)

in which, $R_{10}$, $R_{11}$ and $R_{12}$ could be same or different, which are all —H, —$CH_3$ or —$CH_2CH_3$; m, n and k are numerals selected from any of the positive numbers satisfying the condition of m+n+k equals from 3 to about 30; and wherein Component B3 is a carbonized diimine compound, wherein the carbonized diimine compound is carbonized diimine monomer, poly carbonized diimine or the mixture made up of two or more kinds of carbonized diimine compounds containing 1-30 carbonized diimine groups in their molecular structure with the molecular weight of 40-30000 g/mol at any ration;

wherein the biodegradable polyester is biodegradable.

12. The biodegradable polyester of claim 2, wherein the aliphatic dibasic acid, cyclic aliphatic dibasic acid, esterified derivatives of aliphatic dibasic acid, esterified derivatives of cyclic aliphatic dibasic acid, and mixtures thereof of Component A11 are selected from the group consisting of oxalic acid, succinic acid, glutaric acid, adipic acid, azelaic acid, sebacic acid, tridecanedioic acid, maleic acid, 1,1cyclo-butane-dicarboxylic acid, 1,1-cyclo-hexane diacetic acid, 1,4-cyclo-hexane diacetic acid, cyclo-hexane-1,2, norbornane-2, 3-dicarboxylic acid, amadantane diacetic acid, esters thereof, and mixtures thereof.

13. The biodegradable polyester of claim 9, wherein the aliphatic dibasic acid, cyclic aliphatic dibasic acid, esterified derivatives of aliphatic dibasic acid, esterified derivatives of cyclic aliphatic dibasic acid, and mixtures thereof of Component A11 are dibasic acids or their esters with carbon atom number of $C_4$-$C_{18}$.

14. The biodegradable polyester of claim 9, wherein the aliphatic dibasic alcohol in Component A21 is selected from the group consisting of glycol, 1,2-propanediol, 1,3-propanediol, 1,2-butanediol, 1,4-butanediol, 1,5-pentanediol, 2,2-dimethyl-1,3-propanediol, 2-ethyl-2-tert-butyl-1,3-propanediol, 2,2,4-trimethyl-1,6-hexanediol, and mixtures thereof; and wherein the cyclic aliphatic dibasic alcohol in Component A21 is selected from the group consisting of cyclopentanediol, 1,4-cyclo-hexanediol, 1,2-cyclo-hexanedimethanol, 1,3-cyclo-hexanedimethanol, 1,4-cyclo-hexanedimethanol, isosorbide, and mixtures thereof.

15. The biodegradable polyester of claim 9, wherein the cyclic aliphatic dibasic alcohol in Component A21 is isosorbide or its derivative.

16. The biodegradable polyester of claim 9, wherein the aliphatic polyether dibasic alcohol in Component A21 is selected from the group consisting of ethylene oxide dimer, ethylene oxide trimer, polyethylene oxide, Poly(tetramethylene ether glycol), ethylene oxide-propylene oxide copolymer with the molecular weight between 25-12000 g/mol, and mixtures thereof.

17. The biodegradable polyester of claim 9, wherein the hydroxyl aliphatic acid in Component A21 is selected from the group consisting of glycolic acid, α-hydracrylic acid, β-malic acid, β-hydroxybutyric acid, hydroxy-butanedioic acid, 5-hydroxy-valeric acid, 3-hydroxy-hexanoic acid, 5-hydroxy-hexanoic acid, 6-hydroxy-hexanoic acid, 7-hydroxy-heptanoic acid, 3,5-dihydroxy-heptanoic acid, hydroxy-octanoic acid, 5-hydroxy-decanoic acid, 5-hydroxy-dodecanoic acid, 9,10,16-trihydroxy-hexadecanoic acid, 3,4-dihydroxy-cinnamic acid, p-hydroxy-cinnamic acid, agaric acid, their polymers, and mixtures thereof.

18. The biodegradable polyester of claim 9, wherein the dibasic alcohol containing aromatic nucleus and the polyether dibasic alcohol containing an aromatic nucleus in Component A22 have the molecular structure as shown in Formula 1:

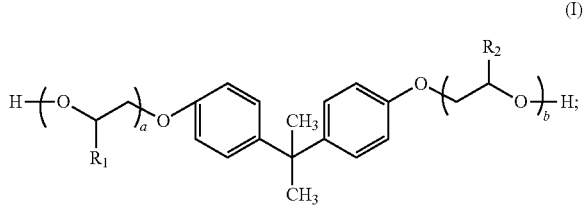

(I)

in Formula I, $R_1$ is —H, —$CH_3$ or —$C_2H_5$; $R_2$ is —H, —$CH_3$ or —$C_2H_5$, and a and b are both numerals selected from any of the positive numbers satisfying the condition of a+b equals from 2 to about 30.

19. The biodegradable polyester of claim 9, wherein the hydroxy organic acid containing aromatic nucleus in Component A22 is selected from the group consisting of o-hydroxybenzoic acid, p-hydroxybenzoic acid, 2,4-dihydroxybenzoic acid, 4-hydroxy phthalate and its derivatives, 4-hydroxy-o-phthalic anhydride, the polymer of the above mentioned organic acids, and mixtures thereof.

* * * * *